(12) United States Patent
Schiewe et al.

(10) Patent No.: US 7,066,171 B2
(45) Date of Patent: Jun. 27, 2006

(54) PROCESS AND APPARATUS FOR PRODUCING INHALABLE MEDICAMENTS

(75) Inventors: Joerg Schiewe, Mainz (DE); Bernd Zierenberg, Bingen (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 89 days.

(21) Appl. No.: 10/340,314

(22) Filed: May 19, 2003

(65) Prior Publication Data

US 2003/0175187 A1 Sep. 18, 2003

Related U.S. Application Data

(62) Division of application No. 10/125,044, filed on Apr. 18, 2002, now Pat. No. 6,663,848.

(30) Foreign Application Priority Data

Apr. 21, 2001 (DE) .......................................... 101 19 718

(51) Int. Cl.
*A61M 11/00* (2006.01)
*A61M 15/00* (2006.01)
*A61M 9/00* (2006.01)

(52) U.S. Cl. ............................ 128/200.14; 128/203.15; 128/203.12; 128/200.19; 422/245.1; 23/273; 62/544; 424/45

(58) Field of Classification Search ............ 128/200.14, 128/203.15, 203.12, 200.19; 422/245.1; 23/273; 62/544; 424/45, 46; 435/135; 540/540; 514/180; 210/34

See application file for complete search history.

(56) References Cited

U.S. PATENT DOCUMENTS 3,801,285 A * 4/1974 Meisenburg et al. ........ 422/254
5,537,832 A * 7/1996 Keus ........................... 62/544
5,921,678 A   7/1999 Desai et al.
6,045,703 A * 4/2000 Miller ......................... 210/659
6,433,166 B1 * 8/2002 Shimazu et al. ............. 540/540
6,444,452 B1 * 9/2002 Keri et al. .................. 435/135

FOREIGN PATENT DOCUMENTS

WO   WO 00/62914       10/2000
WO   WO 01/14036 A1    3/2001

OTHER PUBLICATIONS

International Search Report Reference No. PCT/EP 02/00885.

* cited by examiner

*Primary Examiner*—Gary Kunz
*Assistant Examiner*—M. Haghighatian
(74) *Attorney, Agent, or Firm*—Michael P. Morris; Mary-Ellen M. Devlin; Alan R. Stempel (57) ABSTRACT

A method for crystallizing a substance, especially an inhalable medicament, comprising the following steps:
(a) dissolving said substance in a solvent, to produce a solution of said substance,
(b) producing a segmented stream which consists of alternating segments of said solution of the substance and of a transport medium,
(c) introducing said segmented stream into the first end of a retention stretch, which retention stretch has a first end and a second end, so that said segmented stream passes from said first end to said second end of said retention stretch, and exits from the second end of the retention stretch,
(d) cooling the retention stretch, to thereby bring about crystallization of the substance in the segments of solution, in the segmented stream, as said segmented stream passes through the retention stretch, and
(e) separating the crystals of material from the segmented stream as it exits from the second end of the retention stretch.

Also disclosed is an apparatus for carrying out the method.

1 Claim, 5 Drawing Sheets

PROCESS AND APPARATUS FOR PRODUCING INHALABLE MEDICAMENTS

RELATED APPLICATIONS

This application is a division of Ser. No. 10/125,044 filed Apr. 18, 2002 now U.S. Pat. No. 6,663,848.

BACKGROUND OF THE INVENTION

1. Technical Field

The invention relates to a process for the continuous production of inhalable medicaments and to an apparatus for carrying out the process.

2. Background Information

Within the framework of the invention, the term "medicament" refers to the active component of a medicament which is commonly also referred to as the psychopharmacological agent or active ingredient.

Inhalatives require a certain form of the medicament. For example, micronised medicaments or active ingredients generally come in solid form. In order to guarantee the inhalability of the medicament, high requirements are placed on the particle size, the particle size distribution, the morphology, the stability and the flow performance.

In general, the entire administered dose of the medicament does not reach the lungs, rather only a part of this does. The particle size has a substantial influence on the proportion of the medicament which actually reaches the lungs. For this reason, particles are preferred which have a diameter of less than 20 μm, preferably less than 5 μm and greater than 0.3 μm. The diameter of the particle should be within the given window and furthermore should have the narrowest possible size distribution. Larger particles are separated off during respiration in the upper airways whilst smaller particles are not deposited in the lungs and these leave again when exhaling.

Within the framework of the present invention, particle diameter means the aerodynamic particle diameter wherein this is defined as the equivalent diameter of a ball of density 1 $g/cm^3$ which has the same sedimentation speed in air as the examined particle.

Furthermore, high requirements are placed on the physical stability of the micronised medicament particles. Particles should preferably exist in stable crystalline form with environmental conditions, to prevent agglomeration by phase transition. The stability of the medicament particles thus has indirect influence on the actual quantity of medicaments which reaches the lungs. For this reason, high requirements are placed on the stability of the medicament in order to guarantee consistent quality, especially a particle size or size distribution of the medicament which is constant over time. This quality feature is indispensable in the field of pharmacy and in the use of medicaments because the effect of the medicament depends on the dose which reaches the lungs and thus, as described above, on the particle size and its size distribution.

The same applies for morphology of the micronised particles since the nature of the particle surface has a direct influence on the inclination of the particle towards agglomeration and thus indirect influence on the particle size itself or the durability of the medicament.

Adjuvants can be added to the micronised medicament, allowing the physico-chemical characteristics of a medicament to be set, wherein these influence the quality-determining parameters such as bio-availability, effectiveness and durability in a desired manner.

Apart from the particle size and the size distribution of the micronised medicament, the type, particle size and quantity ratio of the added adjuvant can decisively influence the medicament dose which reaches the lungs.

Conventional processes for producing inhalable medicaments are generally two-stage, when considered from a roughly-structured viewpoint, wherein in a first stage, the medicament is produced in a solid, generally crystalline form which is transformed into micronised particles in a second stage within the framework of a comminution process. Accordingly to the prior art, milling processes can be used for the comminution process, wherein in particular air-jet milling has attained great significance since it is economical, can be used for a multitude of substances and allows simple separation of the desired particle fractions by means of a downstream cyclone separator.

The disadvantage with the air-jet milling used according to the prior art is that the solid material particles are principally subjected to a considerable force effect during the milling process. This force effect induces considerable local heating and moreover leads to the formation of amorphous portions. As a result of the local heating, air-jet milling or milling as a comminution process in general is not suitable for low-melting, thermally unstable or denaturisable materials.

Furthermore, when storing jet-milled medicaments, agglomeration is often observed since the amorphous portions resulting from the milling process re-crystallise.

BRIEF SUMMARY OF THE INVENTION

On this basis, the object of the present invention is to provide a process for the continuous production of inhalable medicaments where it is ensured that the aforementioned requirements of medicaments are maintained, and furthermore the disadvantages of the process used according to the prior art are avoided.

Furthermore, a partial object of the present invention is to provide an apparatus for carrying out the process according to the invention.

A further partial object of the present invention is to provide a medicament which fulfils the requirements of inhalable medicaments, especially the requirements of particle size, particle distribution, morphology and stability.

BRIEF DESCRIPTION OF THE DRAWINGS

FIG. 1 is a diagram depicting the concentration vs. temperature of a solution entering the retention stretch of the apparatus according to the invention.

FIG. 2 depicts the temperature control T(t) of an embodiment of the process according to the invention for setting a constant oversaturation ΔC(t).

FIG. 3 is a schematic embodiment of a micro-reactor for implementing the process of the invention.

FIG. 4 depicts a micro-mixer of the micro-reactor according to a first embodiment of the apparatus according to the invention, in cross-section.

FIG. 4*a* is an enlargement of the structures of the channels of the micro-mixer shown in FIG. 4.

FIG. 5 depicts a segmenter of the micro-reactor according to a first embodiment, in cross-section.

FIG. 6 depicts a micro-mixer of the micro-reactor according to a second embodiment with integrated segmenter, in cross-section.

FIG. 7 depicts a segmenter of the micro-reactor according to a third embodiment, in cross-section.

DETAILED DESCRIPTION OF THE INVENTION

The object, based on the process, is solved by a continuous process for the production of inhalable medicaments which has the following procedural steps:

use of a medicament solution, segmenting the solution by means of a segmenter and a transport medium, induction and guidance of the crystallisation process in a retention stretch by subjecting it to a defined temperature wherein the seed formation process is first induced by means of a rapid temperature reduction in such a way that the solution adopts an oversaturated, meta-stable or unstable state with regard to the temperature T and the concentration C of the material dissolved therein, and following this crystal growth is influenced by intentional cooling, and separating off the crystal particles from the remaining phases in a separator after passing through the retention stretch.

In accordance with the invention, a medicament solution is used as a starting point. Existing medicament solutions can be used, for example a solution which precipitates during the production of the medicament.

This solution is then supplied to a segmenter and is segmented with a transport medium. The transport medium is a second fluid which is immiscible with the solution and with the help of which the solution is divided into the form of separate segments in such a way that the separate segments, which are preferably of the same volume, are inserted into a carrier stream comprising the transport medium. The transport medium can be gaseous or fluid, wherein it has proven to be the case in the tests that air saturated with solvent vapour of the solvent is especially suitable as a transport medium. The two streams which are supplied to the segmenter, i.e. the solution on the one hand and the transport medium on the other hand, leave the segmenter as a segmented, preferably uniformly segmented, two-phase stream.

The dimensions of the segmenter channels of the segmenter which is preferably to be used for the process of the invention lie in the range of 0.1 mm to 5 mm, preferably between 0.2 and 1 mm. Hence these are therefore smallest structures.

Furthermore, the segmenter can be constructively shaped so that its temperature can be easily controlled, that is, it can be easily heated/cooled and great cooling rates—temperature difference per time unit—can be attained. This is supported by the formation of smallest structures.

Furthermore, the flow rate of the solution and transport medium can be varied within wide boundaries, whereupon it is possible to directly influence the formation and thus the shape of the segmented two-phase flow. This can preferably be set so that approximately equivalently-sized fluid segments with a length of two to three times the channel diameter can be produced.

After segmentation, the segmented two-phase flow is supplied to a retention stretch. The retention stretch serves for actual production of the inhalable medicament or the particles which are to be produced with the aforementioned characteristics with regard to particle size, size distribution of the particles, morphology and stability.

When the two-phase flow enters the retention stretch, in a first step the seed formation process is induced by a sharp reduction in temperature. We refer to FIG. 1, which shows the concentration/temperature diagram of the solution, for further explanation of the processes which take place in the retention stretch. Two curves are drawn in the quadrant between the y axis (concentration) and the x axis (temperature) one of which is solid and one which is dotted, and through which three different areas are formed.

Figure 1:
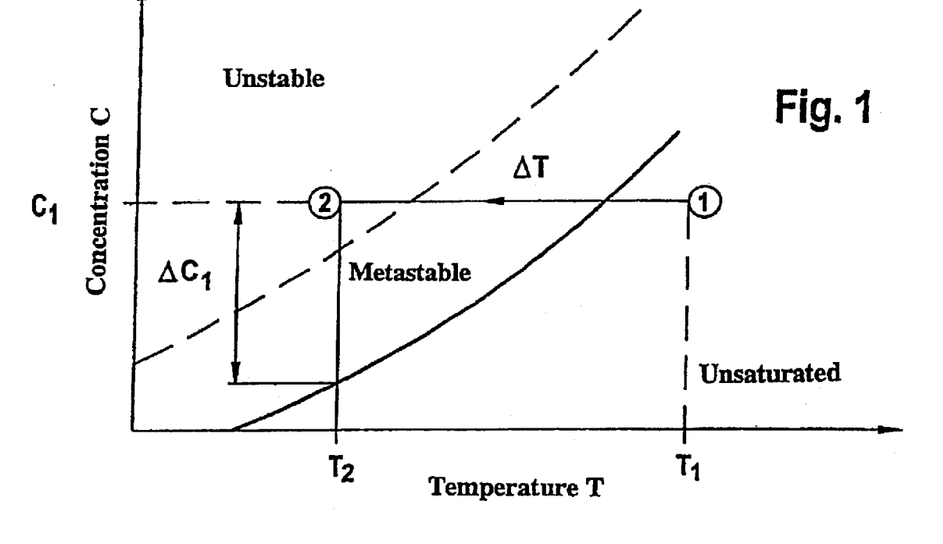

The first area is on the right of the solid line, is therefore limited by this on the left, and represents the area of the unsaturated solution in which neither a seed formation process or crystal growth takes place. Crystal growth, which always requires the prior formation of a seed, basically only takes place in an oversaturated solution since already-formed crystals principally return into solution, at least in part, when crossing the saturation line (solid line).

The area of the oversaturated solution on the left of the solid line can again be divided into two areas wherein the area between the two lines forms the meta-stable zone in which crystal growth but no seed formation process takes place. The third area to the left of the dotted line is the unstable zone in which as the only one of the three areas, a spontaneous seed formation process can take place.

The two-phase flow, or the segments of the solution contained therein, have a concentration $C_1$ when entering the retention stretch, wherein the solution is transferred from a state 1 into a state 2 by means of a sudden reduction in temperature. State 1 can be an unsaturated state or a state which lies in the meta-stable zone, that is, an oversaturated solution can already exist in state 1. In the case of a lack of seeds, it is important for the invention that the state 2 is in the unstable zone, which can be realised according to the invention by a corresponding rapid temperature change. The seed formation process is introduced by transferring the solution into the unstable state and the subsequent crystallisation process is influenced by readjustment of the temperature i.e. by intentional cooling.

If a seed formation process is not required since enough crystallisation seeds are already present, the process can also be carried out when state 2 is in the meta-stable zone.

Targeted influence of crystal growth is only possible by means of the described measures. In accordance with the invention, this contributes substantially to the solution of the object. Very small particles with small diameter in the range of a few micrometers can be obtained in the unstable zone, that is, at very high oversaturation, since a great number of seeds are formed very rapidly, and hardly grow.

For this reason it is necessary to configure the structure of the retention stretch for the process according to the invention in such a way that the temperature can easily be controlled so that it can easily be heated/cooled and that great cooling rates—temperature difference per time unit—can be attained. Hence structures in the range of a few millimeters or micrometers are also suitable in the retention stretch.

In the case of crystallisation according to the prior art, the described manner of proceeding with the sudden shift in status variables is avoided since temperature oscillations are caused in the solution due to crystallisation heat being released in a short period of time, which leads to undefined growth conditions. In contrast to this, with the process of the invention it is possible to exactly control the temperature in the solution at any time by using apparatus with dimensions in the millimeter or micrometer range.

Hence the retention stretch used for the process of the invention has small structures, as already mentioned, wherein the greatest possible surface/volume ratio is desired. For example, the retention stretch is a tube, pipe or channel-shaped retention stretch with a diameter in the range from 0.5 to 10 mm, preferably from 1 mm to 2 mm, wherein according to the length of the retention stretch, which can have dimensions of between 10 cm to 200 m, preferably between 1 m to 25 m, retention times in the range of a few seconds up to several hours can be realised.

The small diameter of the retention stretch, or the great surface/volume ratio, implies a small quantity of solution guided in the retention stretch, which can only store a small amount of heat. For this reason and as a result of the surface/volume ratio, the solution disposed in the retention stretch can be subjected to a defined temperature from outside in a very short time, whereupon a rapid temperature guide is rendered possible. Also due to the small dimensions, only very small temperature gradients are observed in the solution and hence one can assume an extensively homogenous temperature distribution. This is to be stressed since it is important for the effectiveness of the crystallisation that local conditions in the retention stream do not vary and that the desired parameters are set in the entire solution volume.

Contrary to the process used in the prior art, with the process of the invention temperature oscillations do not occur since the temperature in the solution can be set rapidly and in a targeted manner from outside, and since the seed formation process and the crystal growth can be exactly controlled. If the solution was transferred from state 1 to state 2 when using conventional crystallisers corresponding to FIG. 1, in such a way that a high oversaturation occurs, this would cause temperature oscillation which could not be influenced since the seed formation process which takes place in state 2 and the considerable crystallisation heat which results with a high quantity of seeds would shift the state towards higher temperatures, and counter-controlling in the form of cooling would lead to periodic temperature oscillation as a result of the constructive dimensions of conventional crystallisers.

After passing through the retention stretch, the product mixture is supplied to a separator in which the created crystal particles are separated from the remaining phases, so that at the end of the production process, the medicament with the desired characteristics is present after passing through the separator.

Processes are advantageous wherein the medicament solution is prepared by dissolving the solid medicament in a solvent to form such a medicament solution.

Here, the solid medicament is dissolved in a solvent in which it completely dissolves at a given temperature in order to form a medicament solution.

Processes are advantageous wherein
  segmentation of the solution takes place by means of a segmenter and a transport medium with the formation of plug-flow conditions.

An important advantage of this embodiment is that the two-phase flow which exits the segmenter into the tubular retention stretch and which then passes through the retention stretch, does not form a parabolic speed profile (Hagen-Poiseuille law), but rather a rectangular profile formed over time is selected. This differentiates the process of the invention from the processes which occur in conventional crystallisers, wherein a parabolic profile is selected so that the speed in the marginal areas of the pipe is reduced and ultimately becomes zero on the wall.

As a result of this parabolic speed profile, deposits are left on the interior wall of the pipe in conventional crystallisers, especially further-growing crystals, wherein the crystallisers ultimately become blocked or set.

Figure 9:
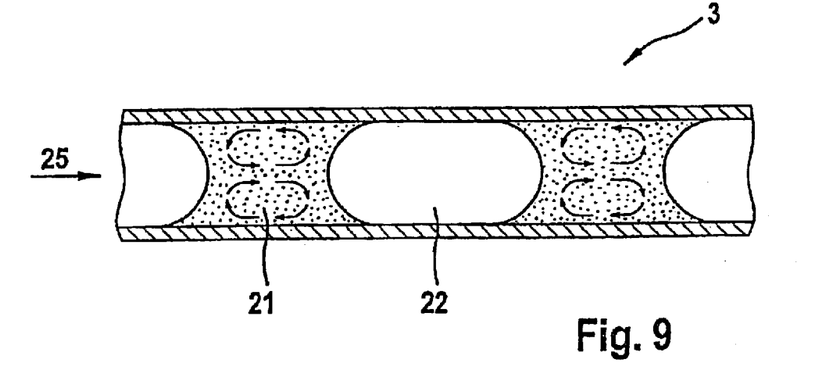
FIG. 9 depicts the retention stretch of an embodiment of a micro-reactor, in cross-section, with the two-phase flow guided in the retention stretch.

With regard to the plug-flow conditions, we refer to FIG. 9 in which the flows or flow directions present in the volume segments are illustrated. The flow processes in the segments support the homogenisation of the solution and counteract the formation of concentration differences in the interior and on the walls. Furthermore, blockage by means of crystalline deposits on the interior walls of the retention stretch are avoided.

Embodiments of the invention are advantageous which are characterised in that
  the medicament solution is blended into a homogeneous precipitation solution in a mixer with a precipitation agent and this precipitation solution passes through the further process.

The precipitation agent is mixed in with the medicament solution in order to reduce the solubility of the medicament in the mixture at a given temperature so that solid particles are formed. Here, this medicament solution is mixed with a precipitating agent in a mixer, in a process step upstream of the segmenter, to produce the most homogeneous precipitation solution possible.

To this end, micro-mixers are especially well suited since mass and heat transport processes take place rapidly and efficiently in them. In the framework of the present invention, micro-mixers mean a structure which has dimensions in the range of 10 μm to 1 mm, preferably between 25 μm to 200 μm.

For production of micronised and inhalable medicaments, a mixture of the medicament solution and the precipitation agent into a precipitation solution of the highest possible homogeneity is necessary. A micro-mixer with its filigree structures is especially suitable for this purpose. When using this, the two fluids, on the one hand the medicament solution and on the other hand the precipitation agent, are separated into individual streams by means of a micro-structure after entering the mixer. The individual streams are, for example, lamellar and are layered with the help of channels disposed in the micro-structure in such a way that a system of thin fluid lamellae results wherein alternately, a fluid lamella of the medicament solution is adjacent to a fluid lamella of the precipitation agent. Here, the lamella density in the micro-mixer is 10 to 1000, preferably 20 to 500 per cm. The fluid system, which is layered in this way and which comprises a multitude of lamellae, is supplied to a mixing chamber in which mixing takes place by diffusion. Mixing according to the principle of diffusion can only take place in acceptably-short times if the structures of the mixer, and hence the lamella thickness of the individual streams, are small enough (preferably 10–200 μm).

The thickness of the fluid lamellae determines, in a decisive manner, the time which is required for compensating for concentration differences by diffusive mixing. If the lamella thickness is in the range of a few tens of micrometers, complete mixing and thus a homogeneity of the precipitation solution can be realised in the entire mixed volume in a time of less than 1 second.

The micro-mixer is preferably configured so that it can easily be heated and/or cooled. Throughflow speed and temperature in the micro-mixer are selected with regard to the seed formation process so that seed formation does not take place in the mixer.

At this point it should be stated that a multitude of devices can be used for heating and cooling the individual described construction elements of the micro-reactor. These are in particular wire resistance heaters, electrical heating foils, Peltier elements and heating and/or cooling devices which operate with a temperature-control fluid such as for example water, oil, air, nitrogen or similar. Alternatively, infra-red radiation and microwave heating can be used.

Also advantageous are embodiments of the micro-reactor wherein on the basis of an etched plate which has an electrical heater, a micro-reactor is implemented in this plate.

Embodiments of the process are advantageous wherein sub-micrometer-sized solid particles are added to form seeds in the segmenter, wherein it is preferred that when using air as a transport medium, the addition of the sub-micrometer-sized solid particles preferably take place by the addition of an adjuvant or the medicament as a powder aerosol in the air stream, and when using a fluid transport medium, sub-micrometer-sized solid particles are added to the transport medium in the form of adjuvant or medicament particles, or when using a fluid transport medium, sub-micrometer-sized solid particles are added to the transport medium in the form of adjuvant colloids.

The crystallisation process can be better controlled by the addition of sub-micrometer-sized solid particles. The working range can be expanded even into the meta-stable range (in the case of lower oversaturation conditions) by the addition of crystal seeds. With the three aforementioned variants for adding the solid particles, the solid particles which serve as crystallisation seeds are added to the segmented solution from outside, i.e. by the transport medium, in the case of the two-phase flow created in the segmenter.

Embodiments of the process are advantageous wherein sub-micrometer-sized solid particles are added in the mixer for seed formation, wherein it is preferred that the addition of the sub-micrometer-sized solid particles takes place by using a precipitation agent which contains colloid particles.

Figure 2:
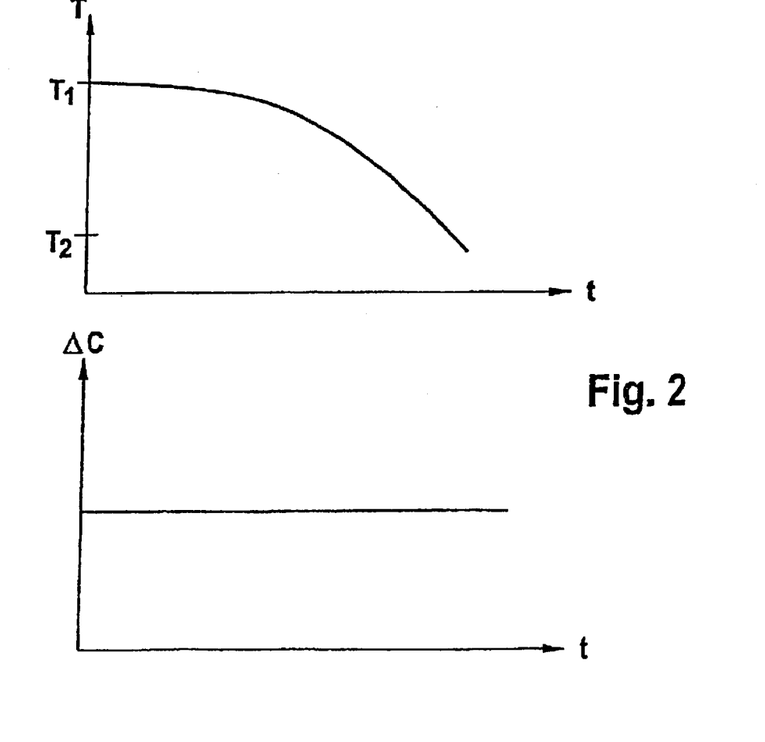

Embodiments of the process are advantageous wherein the temperature control in the retention stretch takes place in such a way that a substantially constant oversaturation $\Delta C_1$ occurs in the solution. This contributes to solving the object of the invention, namely the formation of very small particles or crystals of small diameter. FIG. 2 shows how the temperature T(t) is to be controlled in order to attain constant oversaturation over time, in the case of a parabolic course of concentration (FIG. 1) and assuming diffusion-controlled crystal growth (also FIG. 2).

The partial object relating to the apparatus is solved by a micro-reactor with micro-mixer, a segmenter and a retention stretch, wherein the dimensions of the micro-mixer for separating the added fluids, which are to be mixed, lie in the range of 10 μm to 1 mm, preferably between 25 μm to 200 μm, the dimensions of the channels of the segmenter lie in the range from 0.1 mm to 5 mm, preferably in the range between 0.2 mm and 5 mm, and the retention stretch is configured to be tube-, pipe- or channel-shaped with diameters of its channels in the range from 0.5 to 10 mm, preferably 1 mm to 2 mm, and with the length of between 10 cm and 200 m, preferably 1 m and 25 m.

It can be necessary to use a plurality of micro-reactors for the production of corresponding quantities of the inhalable medicament. Here, for example, 10 to 100 of such micro-reactors are combined into an array, wherein these are operated independently of one another or dependent on one another in parallel. Production quantities of 0.5 to 2 kg per day can be realised with such batteries.

Within such a battery there is a possibility for using only one heating or cooling apparatus which heats or cools all functionally-similar individual devices.

As a result of its micro-structures, the micro-reactor itself does not necessarily have to have small dimensions. The micro-reactor can rather be a technical apparatus in which the functional micro-structures of the type described are implemented.

The partial object of the present invention relating to the preparation of an inhalable medicament which fulfils the requirements of an inhalable medicament is solved by a medicament with an aerodynamic diameter of less than 20 μm, preferably less than 5 μm and greater than 0.3 μm, which is characterised in that it is produced according to the process of the invention.

The invention is explained in greater detail with reference to various embodiment examples according to the drawings, which have already been briefly described above.

The following table provides a key to the various reference numbers used in the drawings.

| Reference Number | Description |
| --- | --- |
| 1 | Micro-mixer |
| 2 | Segmenter |
| 3 | Retention stretch |
| 4 | Aluminium profile |
| 11 | Medicament solution |
| 12 | Precipitation agent |
| 13 | Micro-structure |
| 14 | Mixing chamber |
| 15 | Inlet opening |
| 16 | Inlet opening |
| 17 | Outlet opening |
| 21 | Precipitation solution |
| 22 | Transport medium |
| 23 | Inlet opening |
| 24 | Inlet opening |
| 25 | Two-phase flow |
| 26 | Outlet opening |
| 27 | Large pipe |
| 28 | Small pipe |
| 131 | Supply channels |
| 132 | Supply channels |

FIGS. 1 and 2 have already been explained in detail above. The following is a detailed explanation of the remaining drawings.

Figure 3:
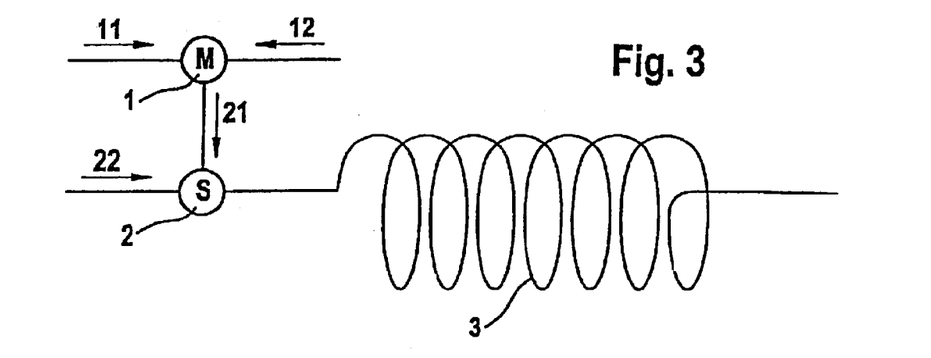

FIG. 3 schematically shows the structure of a micro-reactor for implementing a first variant of the process. The micro-reactor comprises a micro-mixer 1, a segmenter 2 and a retention stretch 3. Here, the medicament solution 11 is first mixed with a precipitation agent 12 in the micro-mixer 1 to form the most homogeneous precipitation solution 21 possible. This precipitation solution 21 is supplied to the segmenter 2 and is segmented with the help of a transport medium 22. The two-phase flow which is present after passing through the segmenter is supplied to the retention stretch 3 in which crystallisation takes place.

Figure 4:
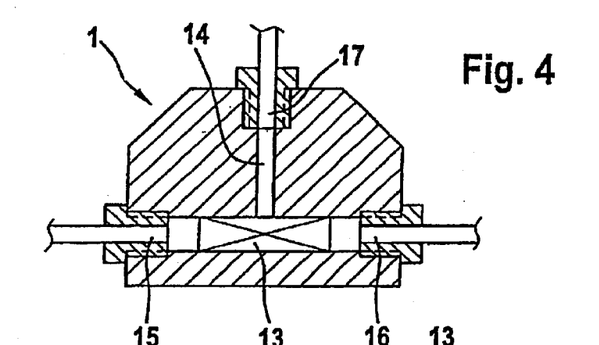

FIG. 4 shows the principle structure of a micro-mixer 1 with the entrance openings 15 and 16 for supply of the medicament solution 11 on the one hand the precipitation agent 12 on the other hand, and the outlet 17 through which the precipitation solution 21 created in the micro-mixer 1 leaves the micro-mixer. The microstructure 13, via which the arriving fluid streams 11 and 12 are divided into individual streams is disposed between the entrance openings 15 and 16. The actual mixing chamber 14 is disposed above this microstructure 13. Mixing into a homogenous solution by means of diffusion takes place in this mixing chamber 14.

Figure 4A:
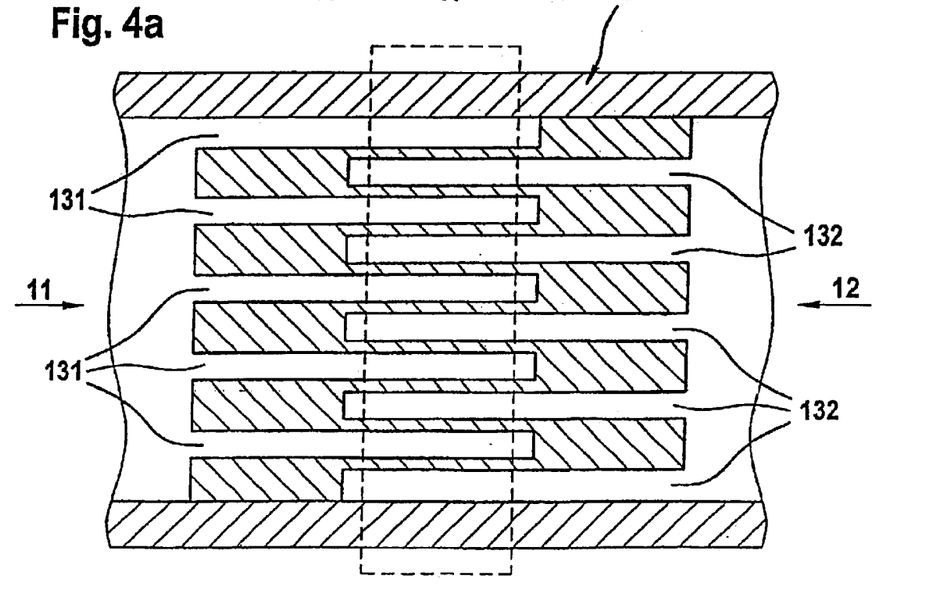

FIG. 4*a* shows an enlargement of the microstructure 13 which lies between the entrance openings 15 and 16. The supply channels 131 and 132 for supplying the fluid streams to the mixing chamber 14 and for dividing the arriving fluid streams into partial streams are arranged in such a way that the partial streams which are separated by them form an alternating system of thin fluid lamellae, wherein in other words, fluid lamellae of the medicament solution 11 and fluid lamellae of the precipitation agent 12 are alternately layered.

Figure 5:
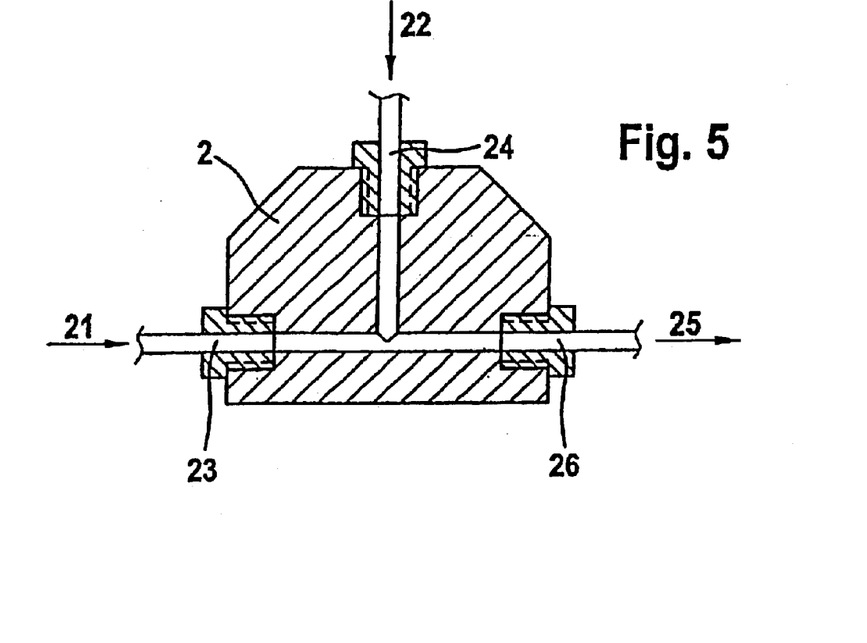

FIG. 5 shows a schematic elevation of the structure of a segmenter 2 with the entrance openings 23 and 24 and the outlet opening 26. The precipitation solution 21 which is supplied to the segmenter 2 via the inlet opening 23 is segmented with the help of the transport medium 22 which is supplied through the inlet opening 24 and leaves the segmenter 2 as a two-phase flow 25.

Figure 6:
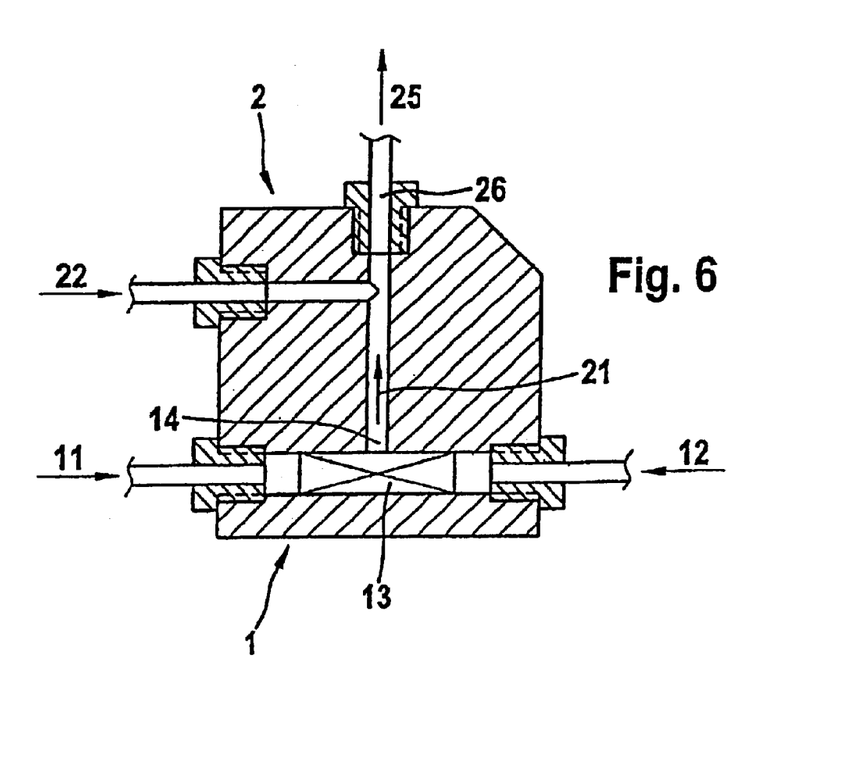

FIG. 6 shows a second embodiment example of a micro-mixer 1 with an integrated segmenter 2. The fluid streams which enter the micro-mixer 1, the medicament solution 11 on the one hand and the precipitation agent 12 on the other hand pass through the micro-structure 13 of the micro-mixer 1 into the mixing chamber 14 and are supplied to segmenter 2 after mixing in the mixing chamber 14 as an extensively homogenous precipitation solution 21. The precipitation solution 21 is segmented in the segmenter 2 with a second fluid which is immiscible with the precipitation solution 21 which serves as a carrier medium 22, wherein the thus-created two-phase flow 25 leaves the segmenter 2 through the outlet opening 26.

Figure 7:
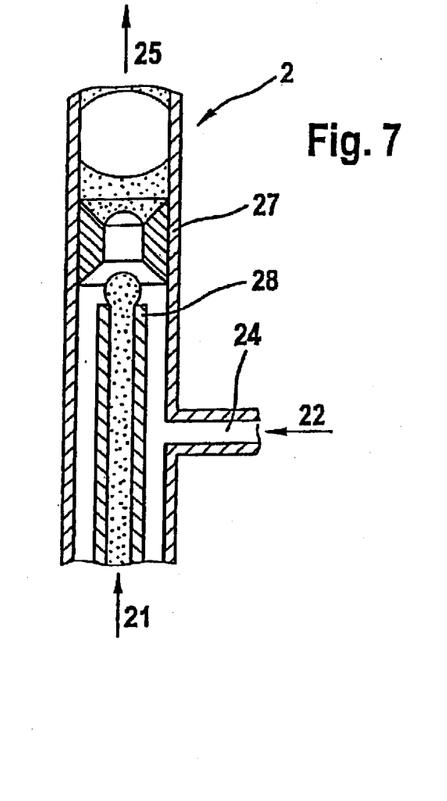

FIG. 7 shows a segmenter 2 which comprises two pipes 27, 28 of which the smaller pipe 28 is disposed within the larger pipe 27 and coaxial thereto. Here, the precipitation solution 21 is fed into the large pipe 27 via the small pipe 28 and is segmented by the transport medium 22 which is supplied laterally through the inlet opening 24 so that a two-phase flow 25 leaves the segmenter 2 at the end of the large pipe 27.

Figure 8:
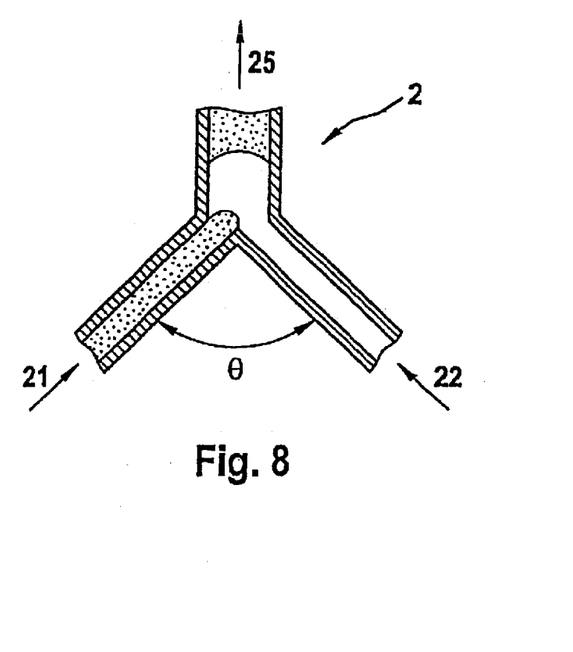
FIG. 8 depicts a segmenter of the micro-reactor according to a fourth embodiment, in cross-section.

FIG. 8 shows a further embodiment example of a segmenter 2 where the supply channels which supply the precipitation solution 21 on the one hand and the transport medium 22 on the other hand form an angle θ which can vary between 0 and 180° and which is 90° in the embodiment example shown in FIG. 8.

FIG. 9 shows a section of a tube-shaped retention stretch 3 in cross-section. The structure of the two-phase flow 25 supplied to the retention stretch 3 is shown. This comprises fluid volumes of precipitation solution 21, preferably of equal sizes, which are segmented with the help of the transport medium 22.

Also shown in FIG. 9 are the flow processes or the associated flow directions which occur during segmenting of the precipitation solution 21. The speeds which are determined over time give a uniform rectangular profile over the cross-section of the pipe of the retention stretch 3. It can be seen that no deposits can form on the interior walls of the pipe of the retention stretch 3 under the flow conditions prevailing in the fluid segment.

Figure 10:
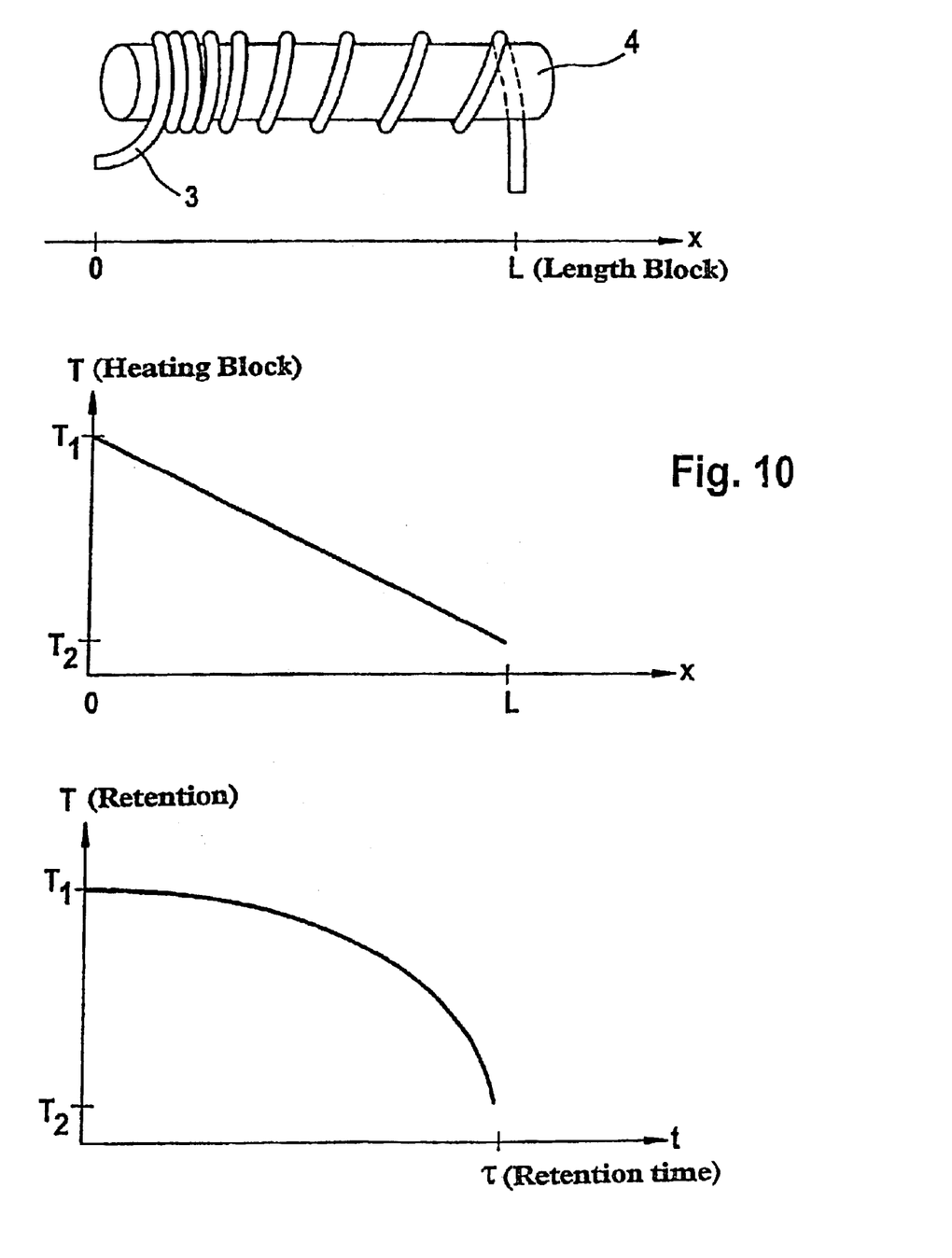
FIG. 10 depicts a retention stretch of an embodiment of a micro-reactor with the temperature courses over the length of the retention stretch and over time.

FIG. 10 shows an embodiment example of a retention stretch in perspective elevation wherein a tube-shaped retention stretch 3 is wound onto a cylindrical aluminium profile 4. The retention stretch 3 can be cooled or heated via the aluminium profile 4.

As already mentioned, it is an embodiment of the process to realise a substantially constant oversaturation $\Delta C_1$ (see FIG. 2, below) in the solution in the retention stretch. This is attained with a temperature profile wherein the temperature gradient increases over time (see FIG. 2, top, and FIG. 10, bottom).

This temperature course T(t) is realised on the one hand by the pitch of the retention stretch 3 on the aluminium block 4 (see FIG. 10, top) and on the other hand by the temperature profile T(L) in the aluminium block 4 (see FIG. 10, centre), wherein in the present example the temperature in the aluminium block 4 decreases in a linear manner and the pitch of the retention stretch 3 wound on the aluminium block increases.

The pitch of the wound retention stretch and the temperature course T(L) in the aluminium block 4 are to be adapted to each individual case. They are dependent on the medicament used, the solution, the addition of solid particles as crystal seeds and the precipitation agent, if used.

In the following text, examples are listed for the active ingredients, the adjuvants, the solvent and the precipitation agent.

The following are used as medicaments or active ingredients:

as anticholinergics; ipratropiumbromide, tiotropiumbromide, tiotropriumbromide-monohydrate, as betasympathomimetics: bambuterol, biolterol, carbuterol, formoterol, clenbuterol, fenoterol, hexoprenalin, procaterol, ibuterol, pirbuterol, tulobuterol, reproterol, salbutamol, sulfonterol, terbutalin, orciprenalin, 1-(2-fluoro-4-hydroxy-phenyl)-2-[4-(1-benzimidazolyl)-2-methyl-2-butylamino]ethanol,erythro-5'-hydroxy-8'-(1-hydroxy-2-isopropylaminobutyl)-2H-1,4-benzoxazin-3-(4H)-one, 1-(4-amino-3-chloro-5-trifluoromethyl-phenyl)-2-tert.-butyl-amino)ethanol, 1-(4-ethoxycarbonylamino-3-cyano-5-fluorophenyl)-2-(tert.-butylamino)ethanol, as antiallergics: disodiumchromeglicate, nedocromil, epinastin, and as steroids: flunisolide, dexamethasone-21-isonicotinate, seratrodast, mycophenolate mofetil, pranlukast, zileuton, butixocort, budesonide, deflazacort, fluticasone, proedrol, mometasin furoate, tipredan, beclometasone (or the 16,21-dipropionate), beclomethasone, Douglas, icomethasone enbutate, cyclometasone, cloprednol, fluocortin butyl, halometasone, deflazacort, alclometasone, cyclometasone, alisactide, prednicarbate, hydrocortisone-butyratepropionate, tixocortolpivalate, alclometaszone-dipropionate, lotrisone, canesten-HC, deprodone, fluticasone-propionate, methylprednisolone-aceponate, halopredone-acetate, mometasone, mometasone-furoate, hydrocortisone-aceponate, mometasone, ulobetasol-propionate, aminogluethimide, triamciolone, hydrocortisone, meprednisone, fluorometholone, dexamethasone, betamethasone, medrysone fluclorolone acetonide, fluocinolone acetonide, paramethasone-acetate, deprodon propionate, aristocort-diacetate, fluocinonide, mazipredone, difluprednate, betamethasone valerate, dexamethasoneisonicotinate, beclomethasonedipropionate, fluocortoloncapronate, formocortal, triamcinolon-hexacetonide, cloprednol, formebolone, clobetasone, endrisone, flunisolide, halcinonide, fluazacort, clobetasol, hydrocortisone-17-butyrate, diflorasone, fluocortin, amcinonide, netamethasone dipropionate, cortivazole, betamethasoneadamantoate, fluodexane, trilostan, budesonide, clobetasone, demetex, trimacinolone benetonide, 9.alpha.-chloro- 6.alpha.-fluoro-11.beta. 17.alpha.-dihydroxy-16.-alpha.-methyl-3-oxo-1,4-androstadiene-17.beta.-carboxy acid methylester-17-propionate.

Other medicaments produced with the process according to the invention are montelukast and pramipexol.

As adjuvants for inhalatives, especially lactose, glucose, sucrose, mannitol and/or trehalose are used.

Examples of solvent and precipitation agents, depending on the medicaments which are to be produced, are shown in the following tables, wherein solvents and precipitation agents must be miscible.

For anticholinergics/betasympathomimetics/antiallergics:

| Active Ingredient | Solvent | Precipitating Agents |
|---|---|---|
| Salt forms | Water, methanol | Alcohols (ethanol, propanol, iso-propanol), ketones (acetone, butanone) |
| Free bases | Alcohols (ethanol, propanol, iso-propanol, tert.-butanol), ketones (acetone, butanone) | Water, methanol |

For steroids:

| Active Ingredient | Solvent | Precipitating Agents |
|---|---|---|
| Polars | Ketones (acetone, butanone) | Alcohols (methanol, ethanol) |
| | Alcohols (ethanol, propanol, iso-propanol, tert.-butanol), ketones (acetone, butanone) | Water, methanol |
| | Aromatics (toluene, ethylbenzene) | Alcohols (ethanol, propanol, iso-propanol) |
| Unpolar | Halogen hydrocarbons (dichloromethane, trichloromethane) | Alcohols (ethanol, propanol, iso-propanol), ether (dimethylether, dioxane) |

Examples of transport media are shown in the following tables, dependent on the active ingredients which are to be produced and the solvents which are used, wherein solvents and transport media are not miscible.

| Active Ingredients | Solvents | Transport Media |
|---|---|---|
| Polar | Water, alcohols (methanol, ethanol iso-propanol, tert.-butanol), ketones (acetone,, propanol, butanone) | Fluids: hydrocarbons (benzene, petrolether, cyclohexane, decaline, benzene, toluene, xylene) Gases: air, nitrogen, carbon dioxide, helium, argon |
| Unpolar | Halogen hydrocarbons (dichloromethane, trichloromethane), ether (diethylether, dibutylether), aromatics (toluene, ethylbenzene) | Fluids water, alcohols (methanol), amides (formamide) Gases: air, nitrogen, carbon dioxide, helium, argon |

What is claimed is:

1. A micro-reactor for implementing a process which comprises the following process steps:

(a) producing a medicament solution, (b) segmenting the solution by means of a segmenter and a transport medium, to yield a segmented medicament solution comprising alternating medicament solution and transport medium phases, (c) introducing the segmented medicament solution into a retention stretch, and therein inducting and guiding crystallisation of the medicament from the medicament solution by subjecting the solution to a defined temperature, wherein seed formation is first induced by means of a rapid temperature reduction in such a way that the solution adopts an oversaturated, meta-stable or unstable state with regard to the temperature T and the concentration C of the medicament dissolved therein, and wherein crystal growth is influenced by intentional cooling, and (d) separating off the crystal particles from the medicament solution phases, using a separator, after the segmented medicament solution has passed through the retention stretch, wherein the micro-reactor comprises a micro-mixer, a segmenter and a retention stretch, wherein:

(a) the dimensions of the micro-mixer for dividing the added fluids which are to be mixed is in the range of 10 μm to 1 mm, (b) the dimensions of the channels of the segmenter lie in the range of 0.1 to 5 mm, and (c) the retention stretch is configured to be tube-, pipe- or channel-shaped with diameters of the channels in the range of 0.5 to 10 mm, and with a length between 10 cm and 200 m.

* * * * *